(12) United States Patent
Yao et al.

(10) Patent No.: US 11,771,556 B2
(45) Date of Patent: Oct. 3, 2023

(54) INTERVENTION GUIDANCE DEVICE

(71) Applicant: Lifetech Scientific (Shenzhen) Co., Ltd., Shenzhen (CN)

(72) Inventors: Bin Yao, Shenzhen (CN); Xiangdong Liu, Shenzhen (CN); Wei Jiang, Shenzhen (CN); Huixiong Xie, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 158 days.

(21) Appl. No.: 17/418,618

(22) PCT Filed: Jul. 10, 2019

(86) PCT No.: PCT/CN2019/095419
§ 371 (c)(1),
(2) Date: Jun. 25, 2021

(87) PCT Pub. No.: WO2020/134025
PCT Pub. Date: Jul. 2, 2020

(65) Prior Publication Data
US 2022/0079751 A1 Mar. 17, 2022

(30) Foreign Application Priority Data
Dec. 27, 2018 (CN) .......................... 201811615406.5

(51) Int. Cl.
*A61F 2/24* (2006.01)
*A61B 17/02* (2006.01)
(Continued)

(52) U.S. Cl.
CPC ............ *A61F 2/2427* (2013.01); *A61B 17/02* (2013.01); *A61F 2/2436* (2013.01);
(Continued)

(58) Field of Classification Search
CPC .... A61F 2/2418; A61F 2/2436; A61F 2/2457; A61F 2/2466; A61B 17/02; A61M 25/09
See application file for complete search history.

(56) References Cited

U.S. PATENT DOCUMENTS 10,226,559 B2    3/2019  Schuermann
10,624,771 B2    4/2020  Lu
(Continued)

FOREIGN PATENT DOCUMENTS

CN    101662999 A    3/2010
CN    108056798 A    5/2018
(Continued)

OTHER PUBLICATIONS

Office Action for corresponding European Application No. EP 19 905 159.0.
(Continued)

*Primary Examiner* — Suba Ganesan
(74) *Attorney, Agent, or Firm* — Raymond Sun

(57) ABSTRACT

An intervention guidance device (10) includes a main body portion (100) and a guidance portion (200). The guidance portion (200) has a contracted configuration and an expanded configuration. In the expanded configuration, the guidance portion (200) has a central area (201) and a closed outer edge (202). In the contracted configuration, the outer edge (202) is farther away from the main body portion (100) than the central area (201), and the guidance portion (200) is restorable from the contracted configuration to the expanded configuration. In the intervention guidance device (10), the radial dimension of the guidance portion (200) is larger than the distance between the chordae tendineae, so that an effective access path that does not cross the chordae tendineae can be established, the subsequent implantation of a heart valve prosthesis does not pass through the chordae
(Continued)

tendineae, and the success rate of a heart valve prosthesis implantation surgery can be improved.

15 Claims, 17 Drawing Sheets

(51) Int. Cl.
    *A61M 25/09*     (2006.01)
    *A61B 17/00*     (2006.01)

(52) U.S. Cl.
    CPC .......... *A61F 2/2457* (2013.01); *A61F 2/2466* (2013.01); *A61M 25/09* (2013.01); *A61B 2017/00743* (2013.01); *A61F 2/2418* (2013.01)

(56) References Cited

U.S. PATENT DOCUMENTS

| | | |
|---|---|---|
| 2008/0082165 A1 | 4/2008 | Wilson |
| 2009/0264859 A1 | 10/2009 | Mas |
| 2015/0351908 A1 | 12/2015 | Keranen et al. |
| 2016/0008131 A1 | 1/2016 | Christianson et al. |
| 2017/0312078 A1 | 11/2017 | Krivoruchko |
| 2017/0319333 A1 | 11/2017 | Tegels et al. |

FOREIGN PATENT DOCUMENTS

| | | |
|---|---|---|
| WO | WO2018/089184 A1 | 5/2018 |
| WO | WO2018/089185 A1 | 5/2018 |
| WO | WO201809185 A1 | 5/2018 |

OTHER PUBLICATIONS

International Search Report dated Sep. 27, 2019 for corresponding PCT Application No. PCT/CN2019/095419.
First Office Action dated Jan. 5, 2021 for corresponding China Application No. 201811615406.5, and translation.
Response to First Office Action dated Jan. 5, 2021 for corresponding China Application No. 201811615406.5, and translation.
Second Office Action dated Jun. 9, 2021 for corresponding China Application No. 201811615406.5, and translation.
Response to Second Office Action dated Jun. 9, 2021 for corresponding China Application No. 201811615406.5, and translation.
Notice of Grant dated Sep. 18, 2021 for corresponding China Application No. 201811615406.5, and translation.

INTERVENTION GUIDANCE DEVICE

FIELD

The present disclosure relates to the field of medical devices and in particular to an intervention guidance device.

BACKGROUND

This section provides only background information related to the disclosure, which is not necessarily the prior art.

As shown in FIG. 1, a human heart is divided into a left heart system and a right heart system. The left heart system includes a left atrium LA and a left ventricle LV. The right heart system includes a right atrium RA and a right ventricle RV. The left atrium LA, the left ventricle LV, the right atrium RA, and the right ventricle RV divide the heart into four chambers. Each chamber has a respective "outlet" at which a mitral valve MV, an aortic valve, a tricuspid valve WV, and a pulmonary valve are arranged respectively. The four valves allow the blood pumped by the heart to circulate in the cardiovascular system in the specified direction. The mitral valve MV is located between the left atrium LA and the left ventricle LV and is connected to the papillary muscles in the left ventricle LV by the chordae tendineae. The normal mitral valve MV is able to circulate a certain amount of blood from the left atrium LA to the left ventricle LV during blood circulation, and when the left ventricle LV contracts, two flexible leaflets of the mitral valve MV are closed, thereby preventing blood from flowing back from the left ventricle LV to the left atrium LA. However, various heart diseases and degenerative diseases can lead to dysfunction of the mitral valve MV, causing the mitral valve MV to become abnormally constricted or dilated, resulting in the backflow of blood from the left ventricle LV into the left atrium LA. Therefore, the loss of function and damage of the mitral valve MV can affect the normal operation of the heart, resulting in the gradual weakening of the heart function and even life-threatening.

For the loss of function and damage of the mitral valve MV, there are currently a number of treatment methods and devices for treating mitral valve dysfunction, such as a conventional valve replacement surgery, which is known as an "open heart" surgery. In short, the valve replacement surgery requires opening the chest, using a ventilator, initiating extracorporeal circulation, stopping and opening the heart, and then removing and replacing the patient's mitral valve MV. The valve replacement surgery has a high medical risk due to the complexity of extracorporeal circulation and poor tolerability of elderly patients. Therefore, there is a growing interest in the treatment of the mitral valve MV by interventional means, such as less heart-invasive transcatheter technologies developed for the delivery of replacement mitral valve components, in which a self-expanding prosthetic valve is typically mounted in a compressed state at the end of a flexible catheter and advanced through the patient's blood vessel or body until the prosthetic valve reaches an implantation position, and then the prosthetic valve dilates to the functional size and state thereof at a position of a defective native mitral valve.

As shown in FIG. 2, a mitral valve prosthesis 1 includes a valve skirt 11, a valve stent body 12, leaflets (not shown in figure), and a tether 13. The valve skirt 11 has an outer diameter larger than an opening of a mitral valve MV. The valve skirt 11 is located on the side of a left atrium LA after implantation of the mitral valve prosthesis 1 into the heart. Therefore, the mitral valve prosthesis 1 is "located" on tissue at a mitral valve opening as a whole, and does not fall off from one side of the left atrium LA to the left ventricle LV. The valve stent body 12 is located at a native mitral valve position. The tether 13 is attached to a distal end of the valve stent body 12 and fixed to the position of an apex of the heart. The mitral valve prosthesis 1 may be stably arranged on the tissue at the mitral valve opening, is not easily dislodged from a native mitral valve leaflet, and does little damage to the native mitral valve leaflet. The service life of the mitral valve prosthesis 1 can be prolonged, and the risks of a secondary replacement valve surgery for a patient can be reduced.

As shown in FIG. 3, both ends of chordae tendineae 21 in a left ventricle LV are connected to a papillary muscle 22 and a mitral valve leaflet 23 respectively, and the chordae tendineae 21 and the papillary muscle 22 pull the mitral valve leaflet 23 so that it does not flip toward the left atrium LA, thereby preventing blood in the left ventricle LV from flowing back to the left atrium LA. Since the tether 13 is connected to a tail end of the mitral valve prosthesis 1 in FIG. 2 and a plurality of chordae tendineae 21 are separated from one same papillary muscle 22, a large gap 24 exists between the chordae tendineae 21, so that related devices can easily pass through the gap 24 between the chordae tendineae 21 during the process of establishing an implantation path of the mitral valve prosthesis 1. Since the tether 13 also passes through the gap 24 between the chordae tendineae 21 after the mitral valve prosthesis 1 is implanted at an opening of a mitral valve MV, and the mitral valve prosthesis 1 cannot be placed coaxially at the opening of the mitral valve MV, perivalvular leakage of the mitral valve prosthesis 1 can occur. In addition, in recent years, scholars consider that the chordae tendineae 21 are related to heart murmur, arrhythmia, chest pain, chest tightness, and palpitation. Therefore, it is particularly important to establish a proper implantation path of an artificial heart valve 1 so that an implantation track of the artificial heart valve does not cross the gap 24 between the chordae tendineae 21. Moreover, the proper implantation path of the artificial heart valve can reduce damage to the chordae tendineae 21 caused by the surgery, and the artificial heart valve can be coaxially released at the opening of the mitral valve MV, so that the probability of perivalvular leakage of the artificial heart valve can be reduced.

SUMMARY

An object of the disclosure is to provide an intervention guidance device which can contribute to the establishment of an effective path, and the object of the disclosure is mainly achieved by the following technical solution.

An intervention guidance device includes:

a main body portion; and a guidance portion having a contracted configuration used for delivery and a predetermined expanded configuration, in the expanded configuration, the guidance portion has a central area and a closed outer edge formed by the outward expansion of the central area, and a distal end of the main body portion is connected to the central area; and in the contracted configuration, the outer edge is farther away from the main body portion than the central area, and when the outer edge of the guidance portion extends beyond the plane of a distal end of a delivery tube, the guidance portion is restorable from the contracted configuration to the expanded configuration.

An intervention guidance device includes:

a main body portion; and a guidance portion having a contracted configuration used for delivery and a predetermined expanded configuration, and the guidance portion includes a woven mesh woven by a plurality of mesh wires and a plug used for gathering and fixing the mesh wires at a closed end of the woven mesh, the mesh wires at the closed end of the woven mesh located at a distal end of the woven mesh are fixed to the plug after being bent from the distal end to a proximal end, and the guidance portion is fixedly connected to a distal end of the main body portion through the plug.

The above intervention guidance devices, by providing the guidance portion with the radial dimension larger than the distance between the chordae tendineae, can establish an effective access path that does not cross the chordae tendineae, where the subsequent implantation of a heart valve prosthesis does not pass through the chordae tendineae, and the success rate of a heart valve prosthesis implantation surgery can be improved.

BRIEF DESCRIPTION OF THE DRAWINGS

Various other advantages and benefits will become apparent to those of ordinary skill in the art upon reading the following detailed description of the preferred implementations. The drawings are only for purposes of illustrating the preferred implementations and are not to be construed as limiting the disclosure. In addition, throughout the drawings, the same reference numerals represent the same components. In the drawings.

DETAILED DESCRIPTION OF THE DISCLOSURE

In order that the above objects, features, and advantages of the disclosure can be more readily understood, specific implementations of the disclosure will be described below in detail with reference to the accompanying drawings. In the following description, numerous specific details are set forth in order to provide a thorough understanding of the disclosure. The disclosure may, however, be embodied in many different forms than those herein set forth, and such modifications as would occur to those skilled in the art may be made without departing from the spirit and scope of the disclosure.

It will be understood that when an element is referred to as being "fixed" or "arranged" to another element, it may be directly on another element or an intermediate element may also be present. When an element is referred to as being "connected" to another element, it may be directly connected to another element or an intermediate element may be present at the same time. The terms "vertical", "horizontal", "left", "right" and the like as used herein are for illustrative purposes only and are not meant to be the only implementations.

Unless defined otherwise, all technical and scientific terms used herein have the same meaning as commonly understood by those skilled in the art to which the disclosure belongs. The terms used in the description of the disclosure herein are for the purpose of describing specific implementations only and are not intended to be limiting of the disclosure. The term "and/or" as used herein includes any and all combinations of one or more of the associated listed items.

It should be noted that in the field of intervention medical instruments, an end of a medical instrument implanted in a human or animal body that is closer to an operator is generally referred to as a "proximal end", an end that is further away from the operator is referred to as a "distal end", and the "proximal end" and "distal end" of any component of the medical instrument are defined in accordance with this principle. An "axial direction" generally refers to a longitudinal direction of the medical instrument when being delivered, and a "radial direction" generally refers to a direction of the medical instrument perpendicular to the "axial direction" thereof, and the "axial direction" and "radial direction" of any component of the medical instrument are defined in accordance with this principle.

Figure 1:
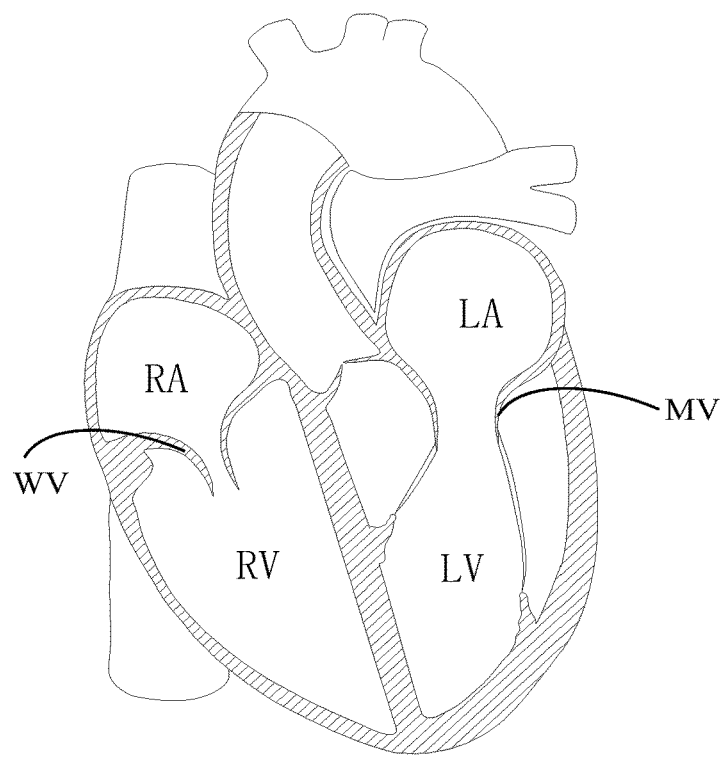
FIG. 1 is a schematic diagram of the structure of various chambers and mitral valves in a heart system.
Figure 2:
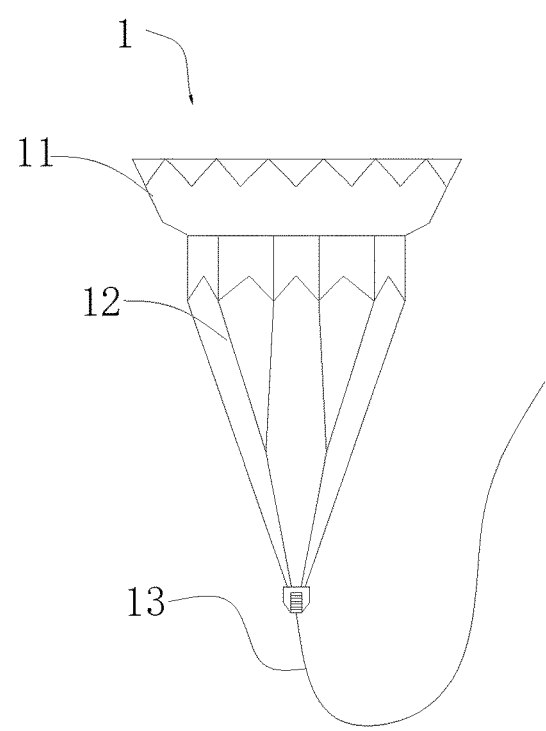
FIG. 2 is a schematic diagram of the structure of a conventional mitral valve prosthesis.
Figure 3:
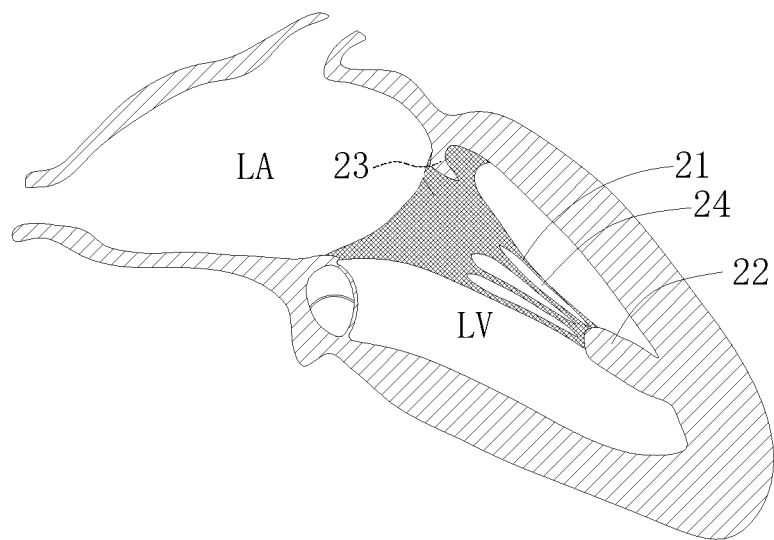
FIG. 3 is a schematic diagram of internal structure of a left atrium and a left ventricle.
Figure 4:
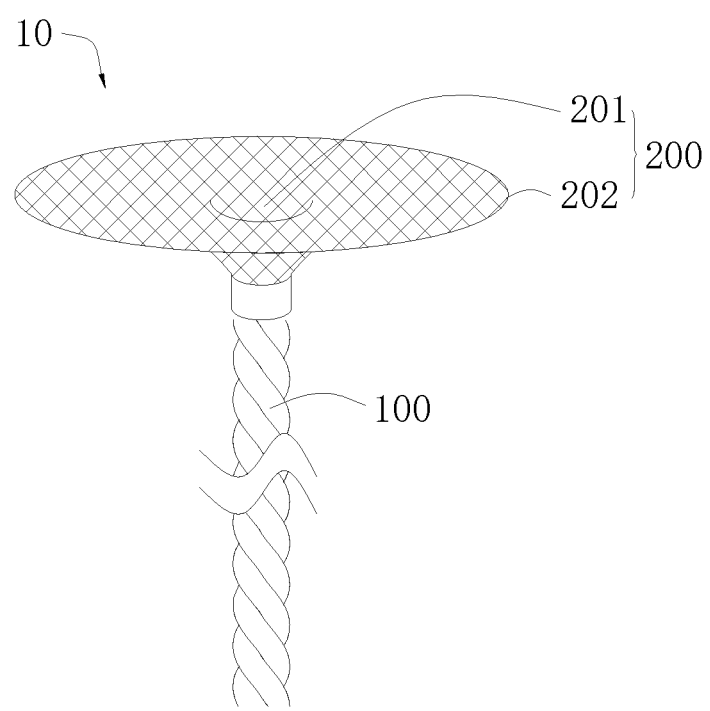
FIG. 4 is a schematic diagram of structure of an intervention guidance device according to an embodiment of the disclosure.

Referring to FIG. 4, an intervention guidance device 10 provided in the disclosure includes a main body portion 100 and a guidance portion 200. The guidance device 200 is connected to a distal end of the main body portion 100.

Figure 7:
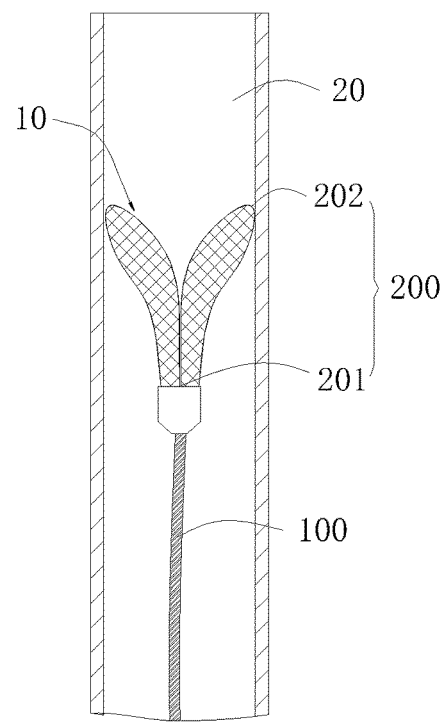
FIG. 7 is a schematic diagram of the structure of the intervention guidance device shown in FIG. 4 loaded into a delivery tube.
Figure 8:
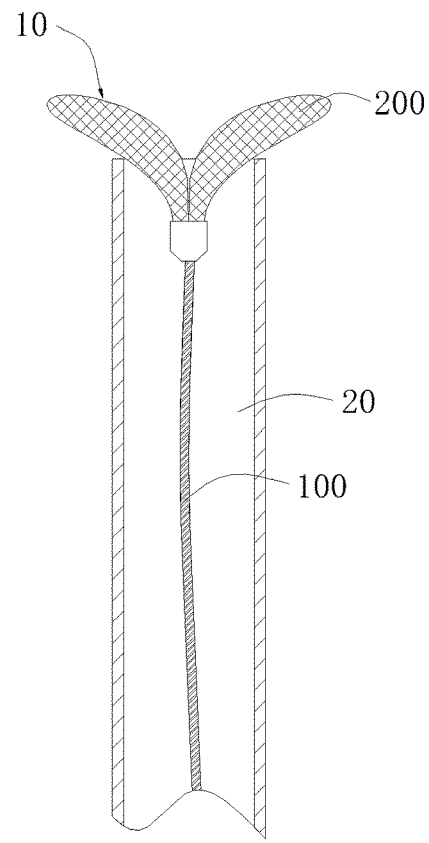
FIG. 8 is a schematic diagram of the structure of the intervention guidance device shown in FIG. 4 being released from the delivery tube.

The guidance portion 200 has a contracted configuration used for delivery and a predetermined expanded configuration. Referring to FIG. 4, in the expanded configuration, the guidance portion 200 has a central area 201 and a closed outer edge 202 formed by the outward expansion of the central area 201, and the distal end of the main body portion 100 is connected to the central area 201. Referring to FIGS. 7 and 8 together, in the contracted configuration, for example in a delivery tube 20, the outer edge 202 is farther away from the main body portion 100 than the central area 201, that is, a maximum radial dimension position in the expanded configuration is in the delivery tube 20 furthest from the main body portion 100. When the main body portion 100 is pushed to cause the guidance portion 200 to move out of the delivery tube 20, and when the outer edge 202 of the guidance portion 200 extends beyond the plane of a distal end of the delivery tube 20, the guidance portion 200 is restorable from the contracted configuration to the expanded configuration. In the present embodiment, the guidance portion 200 is a planar body. Of course, in other embodiments, the guidance portion 200 is not necessarily limited to the planar body, and the guidance portion 200 may be in other configurations. As long as the outer edge 202 of the guidance portion 200 extends beyond the plane of the distal end of the delivery device 20, the guidance portion 200 can be quickly restored from the contracted configuration to the expanded configuration.

It should be noted that when a distance by which the outer edge 202 of the guidance portion 200 may extend beyond the plane of the distal end of the delivery tube 20 is much less than a maximum radial dimension of the outer edge 202 of the guidance portion 200, for example, when the distance by which the outer edge 202 of the guidance portion 200 may extend beyond the plane of the distal end of the delivery tube 20 is less than ½, ⅓, ¼, ⅕, ⅙ or less of the maximum radial dimension of the outer edge 202 of the guidance portion 200, the guidance portion 200 can spring out of the delivery tube 20 and can be restored from the contracted configuration to the expanded configuration. The radial dimension in the disclosure refers to the length of a connecting line of the outer edge 202 across a center point of the central area 201. For example, when the guidance portion 200 is disc-shaped, the radial dimension is a diameter.

In the illustrated embodiments, the outer edge 202 of the guidance portion 200 is also further from the main body portion than the central area 201 in the expanded configuration. More specifically, the plane in which the outer edge 202 of the guidance portion 200 is located is a furthest end surface of the intervention guidance device 10. It will be appreciated that in other embodiments, the outer edge 202 of the guidance portion 200 may also be bent to a proximal end in the expanded configuration, that is, the plane in which the end of the outer edge 202 of the guidance portion 200 is located is not necessarily located in the furthest end surface of the intervention guidance device 10.

In the illustrated embodiments, the central area 201 is recessed from the distal end to the proximal end so as to facilitate rapid restoration of the guidance portion 200 from the contracted configuration to the expanded configuration. In one embodiment, the recess extends to a position connected to the main body portion 100.

Figure 5:
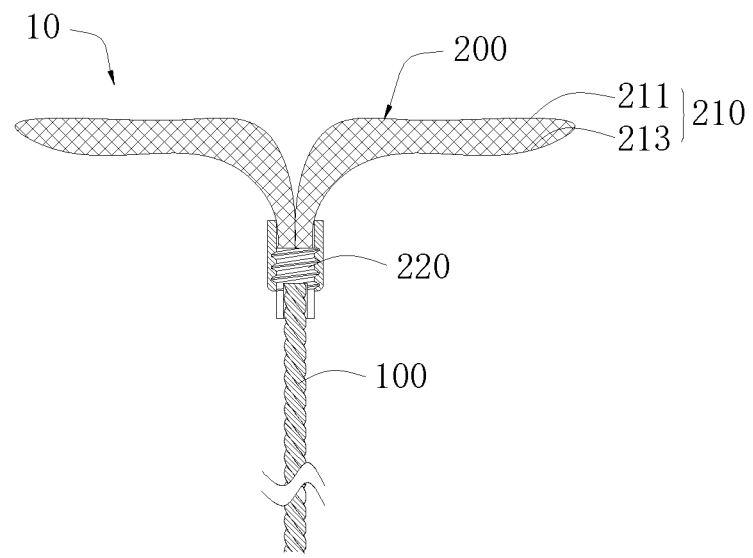
FIG. 5 is a schematic diagram of the structure of the intervention guidance device shown in FIG. 4 from another perspective.

In one embodiment, referring to FIG. 5 together, the guidance portion 200 includes a woven mesh 210 woven by a plurality of mesh wires and a plug 220 used for gathering and fixing the mesh wires at the closed end of the woven mesh 210, the mesh wires at the closed end located at a distal end of the woven mesh 210 are fixed to the plug 220 after being bent from the distal end to a proximal end, and the guidance portion 200 is fixedly connected to the distal end of the main body portion 100 through the plug 220. The mesh wires may be superelastic metal or shape memory metal, such as nitinol.

It will be appreciated that in other embodiments, the plug 220 may be omitted. For example, the mesh wires at the closed end may be gathered and fixed by welding or the like.

In the illustrated embodiments, the woven mesh 210 includes a distal-end mesh surface 211 and a proximal-end mesh surface 213 which are integrally connected. The proximal-end mesh surface 213 is closer to the main body portion 100 than the distal-end mesh surface 211. The mesh wires at the closed end of the distal-end mesh surface 211 pass through the proximal-end mesh surface 213 and then are converged together with mesh wires at the closed end of the proximal-end mesh surface 213, and the converged mesh wires are gathered and fixed by the plug 220. Specifically, the woven mesh 210 may be woven into a cylindrical tubular body by mesh wires. The mesh wires at the closed end of a distal end of the tubular body are reversed to be converged with the mesh wires at the closed end of a proximal end and are closed and fixed by the plug 220 to form a planar body in which the distal-end mesh surface 211 and the proximal-end mesh surface 213 are attached to each other by heat-setting. In one embodiment, the woven mesh 210 is woven from not less than 16 mesh wires, and each mesh wire has a wire diameter of 0.0028 inch to 0.0060 inch. In one embodiment, the woven mesh 210 is woven from 36 to 72 mesh wires to maintain the radial deformability of the woven mesh 210 and to increase an average mesh area of the woven mesh 210. In the illustrated embodiments, the woven mesh 210 is shaped into a planar disc-shaped structure having a diameter of 10 mm to 25 mm. Of course, in other embodiments, the woven mesh 210 can also be shaped into other structures, such as a bowl-shaped structure recessed from the distal end to the proximal end. When the cross section of the woven mesh 210 is not circular, the woven mesh 210 has a radial dimension of 10 mm and 25 mm, that is, a straight line across the central area has a length of 10 mm and 25 mm.

Figure 6:
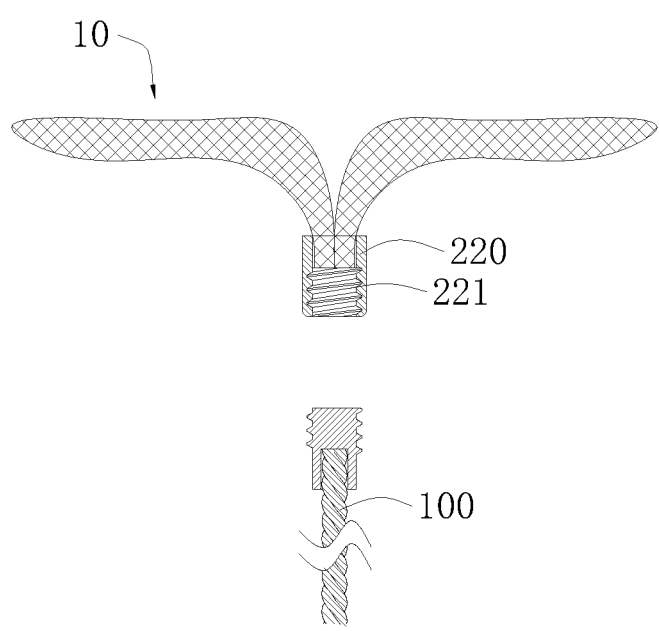
FIG. 6 is an exploded view of the intervention guidance device shown in FIG. 4.

Referring to FIG. 6, the plug 220 is provided with a threaded hole 221 for rotational connection with the main body portion 100. In the illustrated embodiments, the plug 220 is provided with internal threads, and the main body portion 100 is provided with external threads. In other embodiments, the plug 220 may also be provided with external threads, and the main body portion 100 is provided with internal threads. Of course, the main body portion 100 may also be fixedly connected to the plug 220 in other ways, such as welding.

The plug 220 may be made of stainless steel or nitinol. The main body portion 100 may be of a metallic or non-metallic structure. In one embodiment, the main body portion 100 is made of stainless steel or nitinol. The main body portion 100 may have a solid structure. For example, the main body portion 100 may have a rod-like structure formed by a single wire or a cable structure formed by winding a plurality of wires. The main body portion 100 may have a hollow structure. The main body portion 100 may have an outer diameter between 1 mm and 3 mm.

Referring together to FIGS. 7 and 8, when the main body portion 100 passes through the delivery tube 20 and is pulled from the proximal end, the guidance portion 200 may be deformed into the delivery tube 20. At this moment, the outer edge 202 of the guidance portion 200 is located at the furthermost end, and the central area 201 is pulled to the proximal end. When the main body portion 100 is pushed distally, the guidance portion 200 may be quickly restored to the expanded configuration as the outer edge of the guidance portion 200 is pushed out of the delivery tube 20.

It will be appreciated that the guidance portion 200 is not necessarily limited to a woven mesh structure. For example, the guidance portion 200 may also be a body planar structure formed by cutting. As long as the guidance portion 200 just extends out of the delivery tube, the guidance portion 200 may be instantly restored from the contracted configuration to the expanded configuration.

Figure 9:
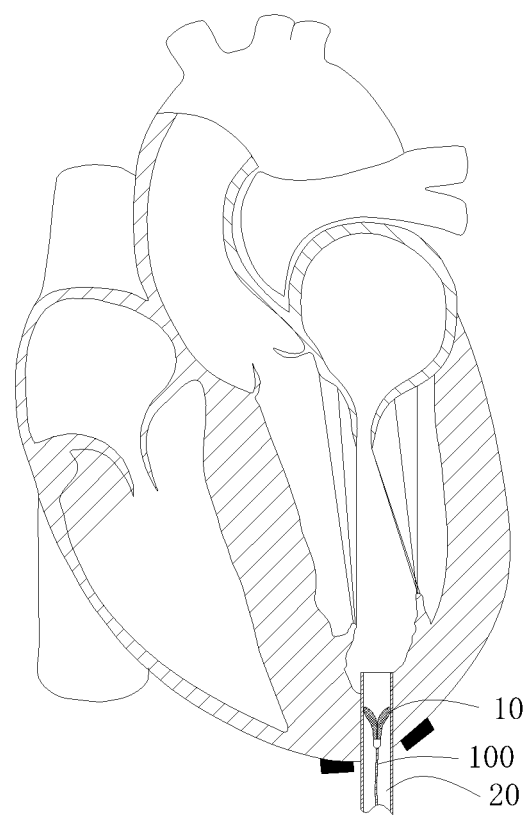
FIG. 9 is a schematic diagram of the structure of the intervention guidance device shown in FIG. 4 loaded into a delivery tube and placed into a ventricle.
Figure 10:
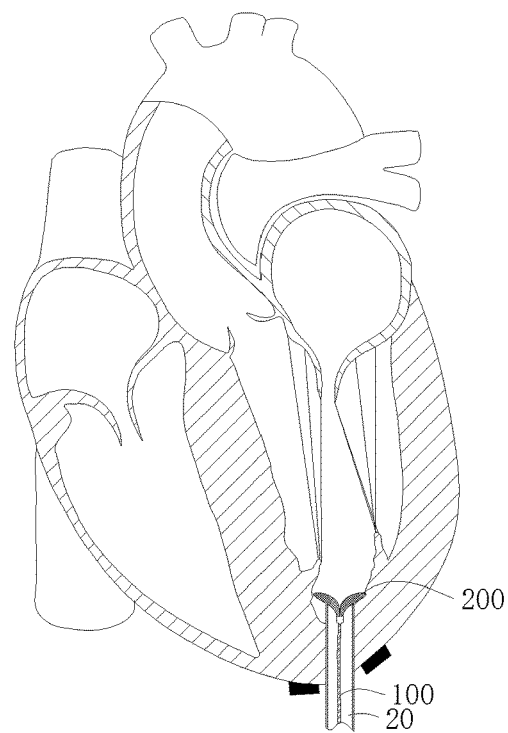
FIG. 10 is a schematic diagram of the structure of the intervention guidance device shown in FIG. 4 after a guidance portion is pushed out of the delivery tube.
Figure 11:
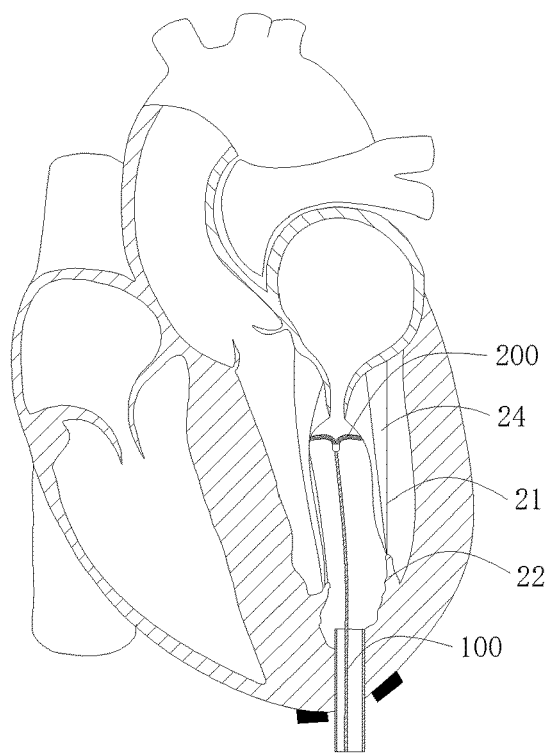
FIG. 11 is a schematic diagram of the structure of the intervention guidance device shown in FIG. 4 being pushed in a left ventricle.
Figure 12:
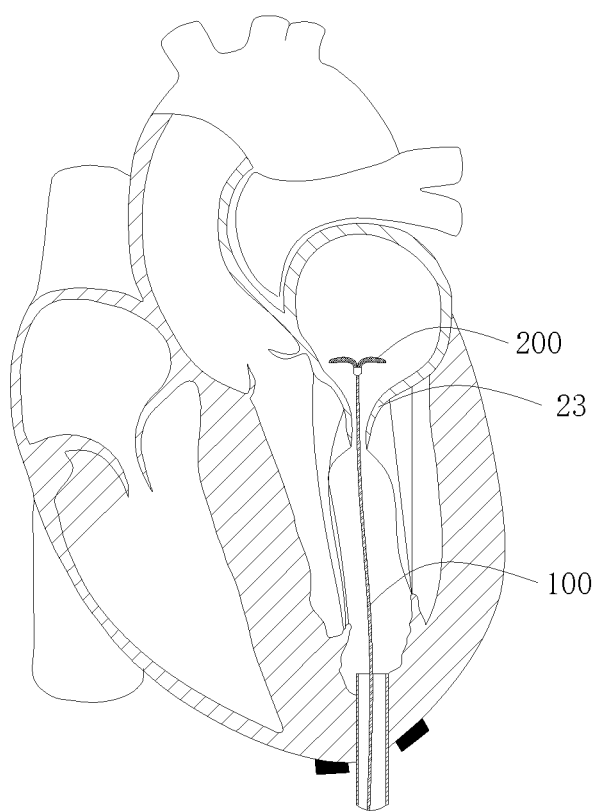
FIG. 12 is a schematic diagram of the structure of the intervention guidance device shown in FIG. 4 after being pushed into a left atrium.

The intervention guidance device 10 may be used as a guide wire for establishing an access track for a mitral valve prosthesis. Referring together to FIGS. 9 and 12, the intervention guidance device 10 is loaded into the delivery tube 20, and the delivery tube 20 enters a left ventricle from an apical position, with the distal end of the delivery tube 20 being at the bottom of the left ventricle. The main body portion 100 is slowly pushed distally, and when the distal end of the guidance portion 200 is pushed out of the delivery tube 20, the guidance portion 200 is quickly restored from the contracted configuration to the expanded configuration, and may adapt to the bottom of papillary muscles and conform to the shape of an inner wall of the heart. In the left ventricle, when the main body portion 100 is pushed distally, the guidance portion 200 may be attached to surrounding tissues and chordae tendineae 21. Since the radial dimension of the guidance portion 200 is larger than a gap 24 between the chordae tendineae 21, the guidance portion 200 does not enter the area between the chordae tendineae 21, and the chordae tendineae 21 pulled by the papillary muscles 22 in the ventricle may be radially pushed away by the guidance portion 200. The main body portion 100 is continuously pushed distally to a mitral valve leaflet 23, and when the left ventricle relaxes, the mitral valve leaflet 23 is in an opened state. Then the main body portion 100 is pushed, and the guidance portion 200 can enter a left atrium through the mitral valve leaflet 23 to establish a vitro-left ventricle-left atrium access path.

In the above intervention guidance device 10, by providing the guidance portion 200 with a radial dimension larger than the distance between the chordae tendineae, an effective access path can be established that does not cross the chordae tendineae, where the subsequent implantation of a heart valve prosthesis does not pass through the chordae tendineae. Therefore, the success rate of a heart valve prosthesis implantation surgery can be improved.

Figure 13:
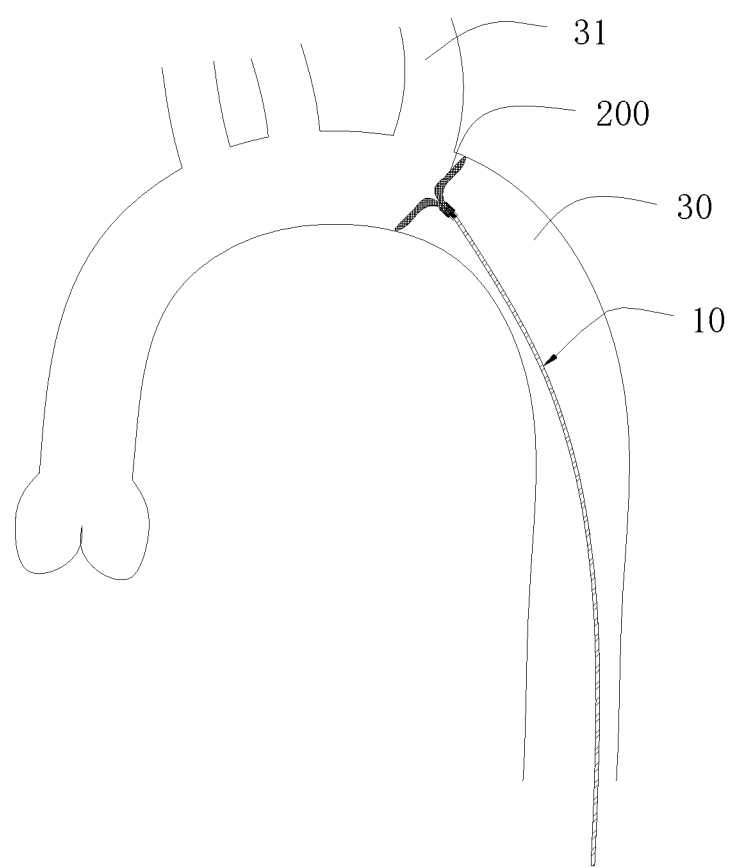
FIG. 13 is a schematic diagram of the structure of the intervention guidance device shown in FIG. 4 being pushed in a blood vessel.
Figure 14:
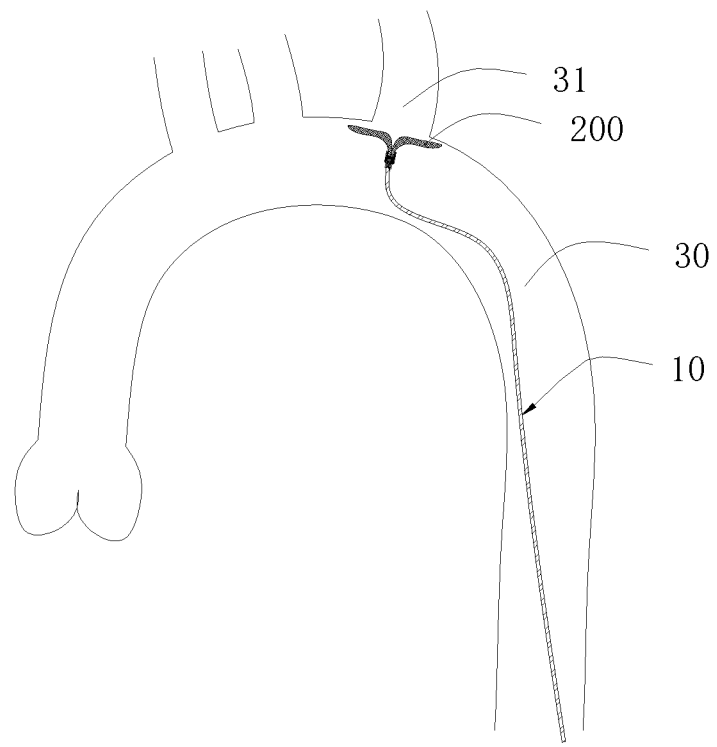
FIG. 14 is a schematic diagram of the structure of the intervention guidance device shown in FIG. 4 at a branch blood vessel.

The intervention guidance device 10 may also be used in a peripheral vascular surgery. In an aortic valve replacement surgery, the intervention guidance device 10 may be used as a guide wire to establish an access path for an aortic valve prosthesis. A general guide wire is often impacted by blood in the process of establishing an access, and a distal end of the guide wire is easily influenced by blood flow to enter a branch blood vessel of an aortic arch part, so that many problems are introduced to the surgery. However, the intervention guidance device 10 of the present disclosure can effectively avoid these problems. Referring to FIGS. 13 to 14, the intervention guidance device 10 enters a descending aorta 30 through an arterial vessel of a lower limb. When the guidance portion 200 encounters a branch blood vessel 31, because the radial dimension of the guidance portion 200 is larger than an opening of the branch blood vessel 31, the guidance portion 200 can avoid the branch blood vessel 31 instead of entering the branch blood vessel 31, thereby smoothly establishing an access path of an aortic valve prosthesis. In addition, the guidance portion 200 can also adapt to the shape of the inner wall of the blood vessel. The image can clearly show the shape of the blood vessel during the access process.

Figure 15:
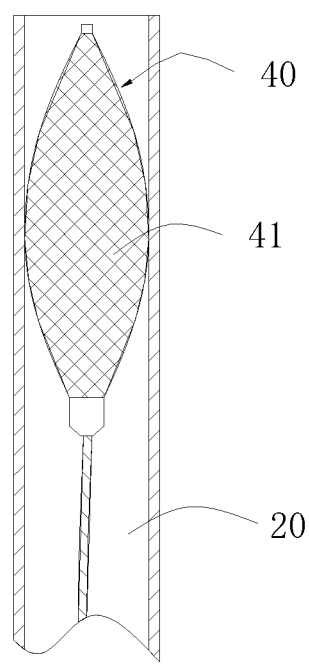
FIG. 15 is a schematic diagram of the structure of an intervention guidance device loaded into a delivery tube in the prior art.
Figure 16:
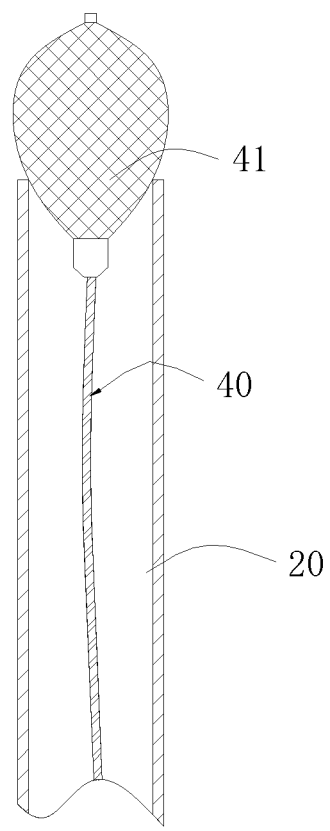
FIG. 16 is a schematic diagram of the structure of the intervention guidance device shown in FIG. 15 released from the delivery tube.
Figure 17:
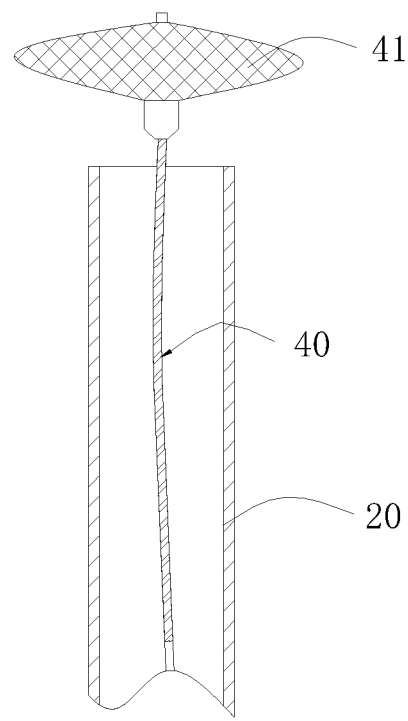
FIG. 17 is a schematic diagram of the structure of the intervention guidance device shown in FIG. 15 after being released from the delivery tube.

It should be noted that some guidance devices for ultrasound intervention are known in the prior art. Referring to FIGS. 15 to 17, an end of an intervention guidance device 40 is generally provided with a mesh-like three-dimensional structure 41 such as a sphere and an ellipsoid in order to be better shown under an ultrasound medium. After the intervention guidance device 40 is loaded into a delivery tube 20, a central area of the three-dimensional structure 41 may be located at two ends, and an outer edge may be located between the two ends. For example, the three-dimensional structure 41 will be contracted to a linear structure. When being pushed distally, the three-dimensional structure 41 needs to be pushed out for a certain distance, so that the distance of the three-dimensional structure 41 extending out of the delivery tube 20 is not less than a distance of a maximum radial dimension of the three-dimensional structure 41. Therefore, the three-dimensional structure 41 can be restored from a contracted state to an expanded state. When the intervention guidance device 40 is applied to an implantation surgery of a valve prosthesis, since the three-dimensional structure 41 needs to be pushed out of the delivery tube 41 for a long distance when the three-dimensional structure 41 is restored from the contracted state to the expanded state, the three-dimensional structure 41 may pass through some chordae tendineae at the bottom of a ventricle before the three-dimensional structure 41 is restored to the expanded state. Therefore, the established access path cannot be prevented from completely avoiding the chordae tendineae. In the intervention guidance device 10 of the disclosure, since a distance of the guidance portion 200 extending out of the delivery tube 20 may be much less than the maximum radial dimension of the outer edge (the extending distance is less than ½ of the maximum radial dimension of the outer edge, or the extending distance may be ignored with respect to the maximum radial dimension of the outer edge), the guidance portion 200 can be instantly restored from the contracted configuration to the expanded configuration. Therefore, the guidance portion 200 can be completely prevented from extending into a gap of the chordae tendineae, thereby improving the success rate of a valve prosthesis implantation surgery.

In addition, because the expanded state of the guidance portion 200 has a large area, the guidance portion 20 may be detected by ultrasound and digital subtraction angiography (DSA) and has wide adaptability. Moreover, the position and shape of tissues are clearly determined by the shape of the guidance portion 200.

Referring to FIGS. 18 to 29, the disclosure also provides a method for implanting a valve prosthesis. The method includes the following steps: S11: an incision is formed in a left chest to expose a ventricle; S12: an access path is established from the ventricle to an atrium using an intervention guidance device 10 and which avoids chordae tendineae; S13: a valve prosthesis 1 is placed along the intervention guidance device 10 at a native valve between the ventricle and the atrium through a valve delivery device 2. The method for implanting a valve prosthesis provided by the disclosure may effectively avoid the gap 24 between the chordae tendineae 21 during the process of establishing an access path of the valve prosthesis 1, so that the phenomenon that a tether 13 on the valve prosthesis 2 passes through the gap 24 between the chordae tendineae 21 can be reduced during the implantation process of the valve prosthesis 2. Therefore, the phenomenon that the valve prosthesis 2 cannot be coaxially placed with the native valve because the tether 13 passes through the gap 24 between the chordae tendineae 21 during the implantation process of the valve prosthesis 2 is reduced, and the phenomenon of perivalvular leakage after the implantation of the valve prosthesis 2 is reduced. Meanwhile, the access path of the disclosure can effectively reduce damage to the chordae tendineae 21 when the tether 13 of the valve prosthesis 2 is hung on the chordae tendineae 21 during the implantation process.

Figure 18:
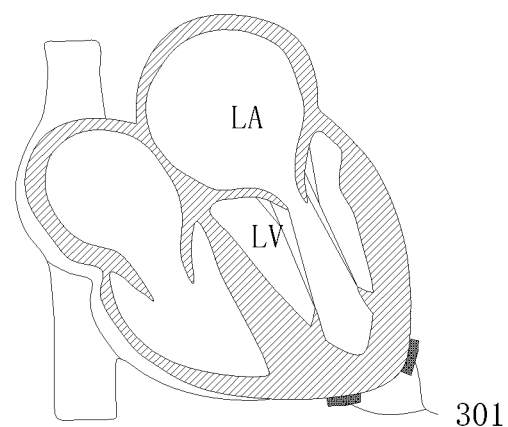
FIG. 18 is a schematic diagram of the structure of forming an apical pericardium on a heart.
Figure 19:
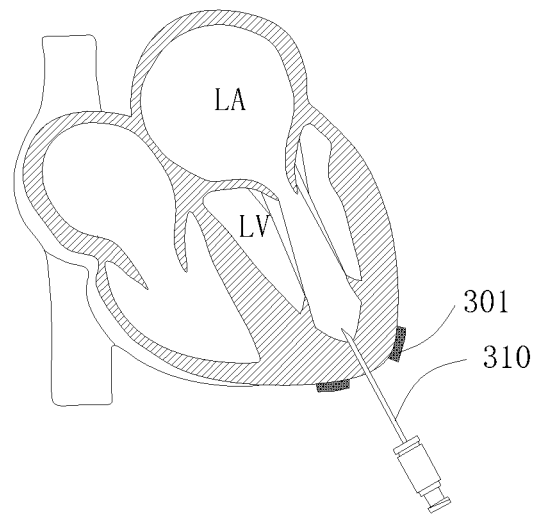
FIG. 19 is a schematic diagram of the structure of an apical puncture needle extending into the left ventricle.
Figure 20:
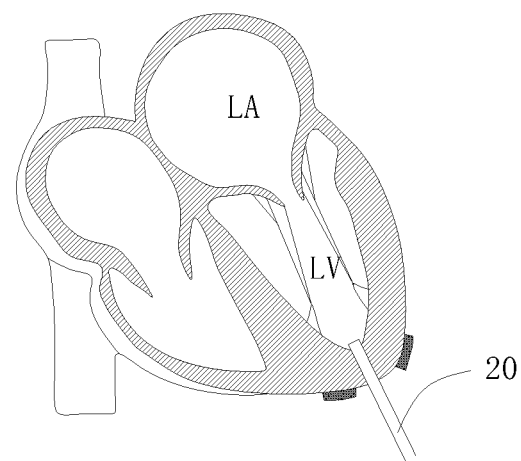
FIG. 20 is a schematic diagram of the structure of the delivery tube extending into the left ventricle.
Figure 21:
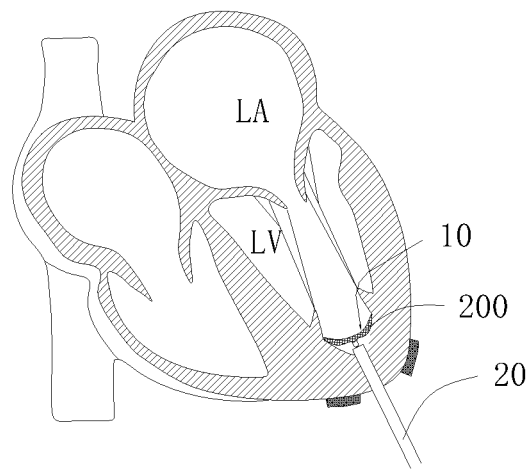
FIG. 21 is a schematic diagram of the structure of the intervention guidance device placed into the delivery tube.

For the convenience of describing the method for implanting an artificial heart valve of the disclosure, the disclosure is described by applying the method for implanting an artificial heart valve to an implantation surgery of the mitral valve prosthesis 1. Referring to FIG. 18, step S11 includes the following steps:

S111, an incision is made in an interval between the fifth and sixth ribs of the left chest, and an apex of a left ventricle LV is exposed after opening a pericardium longitudinally through the incision;

S112, an apical pericardium 301 is sutured at the apex of the left ventricle LV;

When the surgery of the valve prosthesis 2 is completed, tissues at an apical puncture may be pressed together by tightening the apical pericardium 301, which helps to improve the healing effect and the healing speed of the tissues at the apical puncture.

Referring to FIGS. 19 to 24, step S12 includes the following steps:

S121: an apical puncture needle 310 is used to puncture the apex of the left ventricle LV at the position of the apical purse 301 to form a puncture hole;

S122, a delivery tube 20 extends into the left ventricle LV through the puncture of the apical pericardium 301, and a positional relationship between the delivery tube 20 and a ventricular wall is adjusted according to imaging (for example, DSA image) such that a distal end of the delivery tube 20 just enters the left ventricle LV or is exposed within 10 mm;

S123, the intervention guidance device 10 is placed into a tube cavity of the delivery tube 20, and with the aid of imaging (for example, DSA image or ultrasound image), the intervention guidance device 10 is slowly pushed distally into the left ventricle LV so that an outer edge of a guidance portion 200 is just pushed out of the distal end of the delivery tube 20 and is restored to an expanded configuration within the left ventricle LV.

Figure 22:
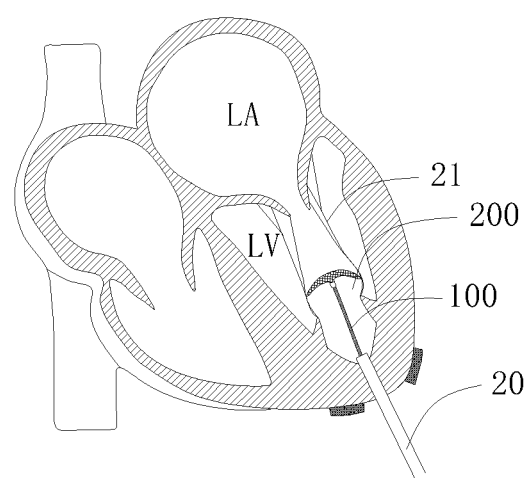
FIG. 22 is a schematic diagram of the structure of the intervention guidance device being pushed into the left ventricle.
Figure 23:
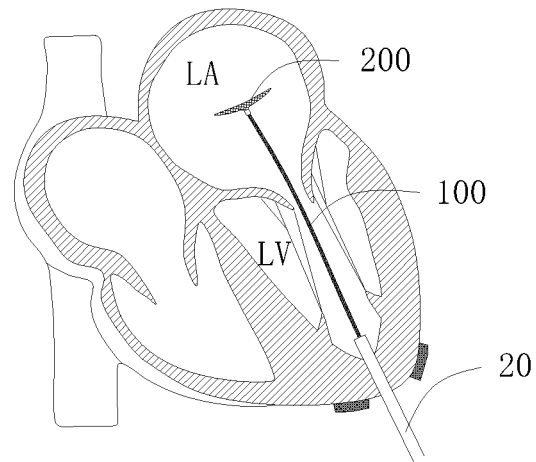
FIG. 23 is a schematic diagram of the structure of the intervention guidance device after being pushed into the left atrium.
Figure 24:
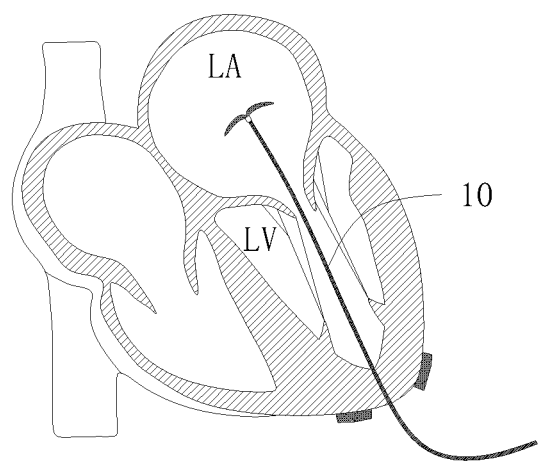
FIG. 24 is a schematic diagram of the structure of an vitro-left ventricle-left atrium track established by the intervention guidance device.
Figure 25:
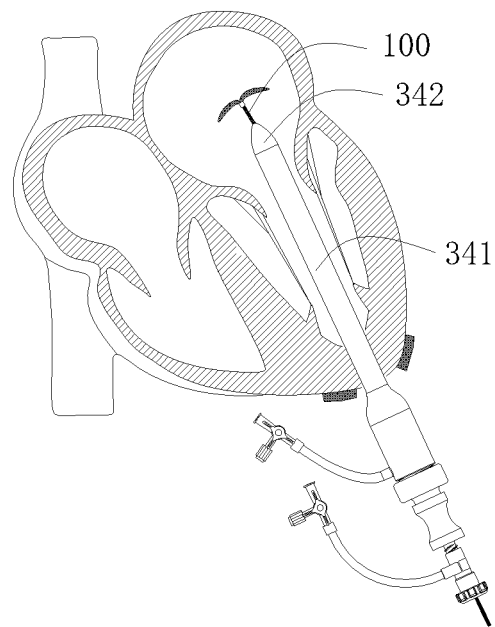
FIG. 25 is a schematic diagram of the structure of an apical dilated sheath and a sheath core extending into the left atrium.
Figure 26:
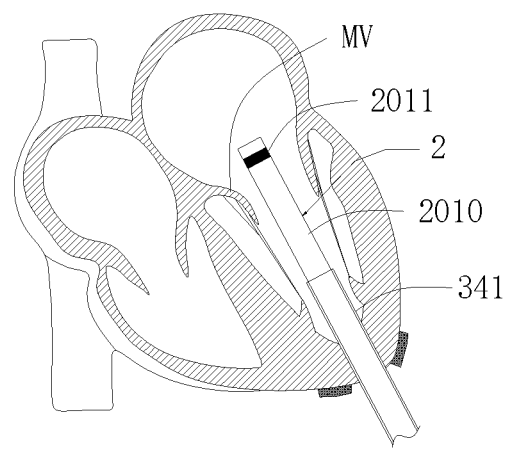
FIG. 26 is a schematic diagram of the structure of a valve delivery device inserted into the left atrium.
Figure 27:
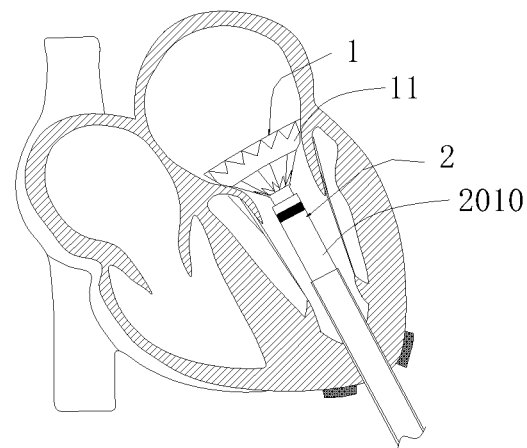
FIG. 27 is a schematic diagram of the structure of a valve prosthesis partially released in the valve delivery device.
Figure 28:
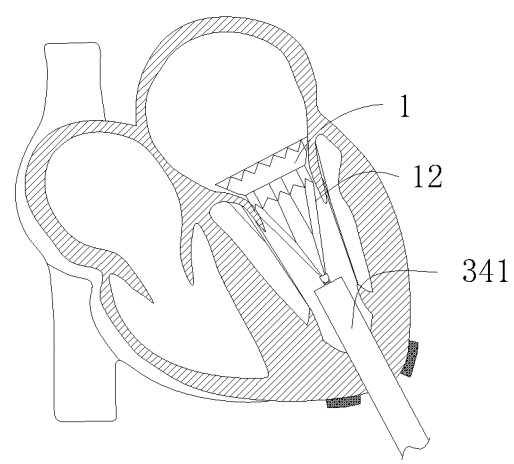
FIG. 28 is a schematic structure view of a valve body of the valve prosthesis after being released from the valve delivery device.
Figure 29:
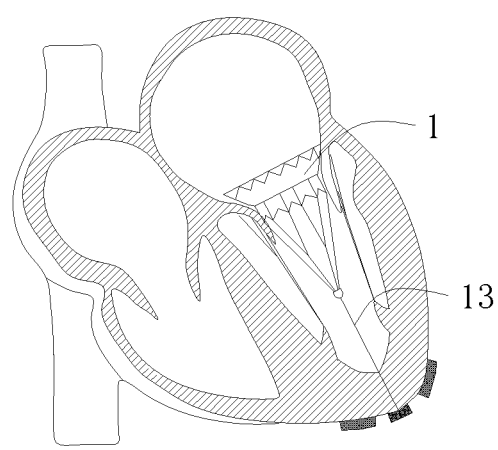
FIG. 29 is a schematic diagram of the structure of the valve prosthesis after implantation.

S124, the intervention guidance device 10 continues to be pushed until the guidance portion 200 is pushed into the left atrium LA. Specifically, the morphologic change of the guide portion 200 is observed with the aid of imaging to see if the distal end of the guidance portion 200 is bent to the proximal end; for example, as shown in FIG. 22, the distal end of the guidance portion 200 is bent to the proximal end by the chordae tendineae 21. After that, the intervention guidance device 10 is withdrawn to the apex. The angle of the delivery tube 20 and a ventricular wall is adjusted, and the intervention guidance device 10 is slowly pushed toward the left atrium LA again. The guidance portion 200 cannot be bent in the pushing process. If it is bent, the intervention guidance device 10 should be withdrawn. The step is repeated until the guidance portion 200 is pushed into the left atrium LA.

S125, the delivery tube 20 is withdrawn, and the intervention guidance device 10 is retained in the heart to obtain a vitro-left ventricle-left atrium track.

Referring to FIGS. 25 to 29, step S13 includes the following steps:

S131, an apical dilated sheath 341 and a sheath core 342 extend along the main body portion 100 into the left ventricle LV, and reach the left atrium LA across the mitral valve MV. The structure of the apical dilated sheath 341 and the sheath core 342 is known in the prior art and will not be described in detail herein.

S132, the apical dilated sheath 341 is fixed, the sheath core 342 and the intervention guidance device 10 are withdrawn from the heart, and the valve delivery device 2 delivers the valve prosthesis 1 to the mitral valve MV through the apical dilated sheath 341.

Specifically, the valve delivery device 2 is placed in the apical dilated sheath 341, and the valve delivery device 2 is slowly pushed, so that a distal end of an outer sheath 2010 of the valve delivery device 2 passes through the mitral valve MV, and a development ring 2011 of the outer sheath 2010 just crosses the mitral valve MV into the left atrium. Then the apical dilated sheath 341 is withdrawn back into the left ventricle LV.

S133, the valve prosthesis 1 is released from the valve delivery device, so that the valve prosthesis 1 is located at the mitral valve MV.

Specifically, when the position of the valve delivery device 2 is confirmed, a handle of the valve delivery device 2 is rotated to withdraw the outer sheath 2010 proximally, so that a valve skirt 11 of the valve prosthesis 1 is unconstrained on the left atrium LA while a valve stent body 12 is still within a cavity of the valve delivery device 2. At this moment, the position of the valve prosthesis 1 after being released on the left atrium LA is observed through a DSA image. If it is found that the release position of the valve prosthesis 1 is inappropriate, the outer sheath 2010 is moved distally so that the valve prosthesis 1 is withdrawn into the outer sheath 2010. The above steps are repeated until it is confirmed that the release position of the valve prosthesis 1 is correct, and then the valve prosthesis 1 is completely released. Then the tether 13 at the proximal end of the valve prosthesis 1 is pulled out of the left ventricle LV by the valve delivery device 2. The valve delivery device 2 and the apical dilated sheath 341 are withdrawn from the heart, the tether 13 is then tightened and fixed to an outer surface of the left ventricle LV, and the apical pericardium 301 at the apex of the left ventricle LV is finally tightened to complete the release of the valve prosthesis 1.

It should be noted that the structure of the valve delivery device 2 in the disclosure can be found in CN201711479941.8, CN201711479996.9, and CN201711487976.6, and will not be described in detail herein.

The various technical features of the above-described embodiments may be combined in any combination, and in order to simplify the description, all possible combinations of the various technical features in the above-described embodiments are not described. However, as long as the combinations of these technical features do not contradict, they should be considered to be the scope of the description.

The above-described examples express only a few implementations of the disclosure, which are described in greater detail but are not to be construed as limiting the scope of the disclosure. It will be appreciated by those of ordinary skill in the art that numerous variations and modifications may be made to the disclosure without departing from the concept of the disclosure, which fall within the protection scope of the disclosure. Therefore, the protection scope of the disclosure should be determined by the appended claims.

The invention claimed is:

1. An intervention guidance device, comprising:
a main body portion; and
a guidance portion having a contracted configuration used for delivery and a predetermined expanded configuration, in the expanded configuration, the guidance portion has a central area and a closed outer edge formed by the outward expansion of the central area, and a distal end of the main body portion is connected to the central area; and in the contracted configuration, the outer edge is farther away from the main body portion than the central area, and when the outer edge of the guidance portion extends beyond a plane of a distal end of a delivery tube, the guidance portion is restorable from the contracted configuration to the expanded configuration wherein the guidance portion is a planar body.

2. The intervention guidance device according to claim 1, wherein, in the expanded configuration, the radial dimension of the guidance portion is larger than a gap between the chordae tendineae of the human heart.

3. The intervention guidance device according to claim 2, wherein the central area is recessed from the distal end to the proximal end.

4. The intervention guidance device according to claim 3, wherein the recess extends to a position connected to the main body portion.

5. The intervention guidance device according to claim 2, wherein the outer edge of the guidance portion is bent to a proximal end in the expanded configuration.

6. An intervention guidance device, comprising:
a main body portion; and
a guidance portion having a contracted configuration used for delivery and a predetermined expanded configuration, in the expanded configuration, the guidance portion has a central area and a closed outer edge formed by the outward expansion of the central area, and a distal end of the main body portion is connected to the central area; and in the contracted configuration, the outer edge is farther away from the main body portion than the central area, and when the outer edge of the guidance portion extends beyond a plane of a distal end of a delivery tube, the guidance portion is restorable from the contracted configuration to the expanded configuration;
wherein the guidance portion comprises a woven mesh woven by a plurality of mesh wires and a plug used for gathering and fixing the mesh wires at a closed end of the woven mesh, the plug is located in the central area, and the mesh wires at the closed end of the woven mesh located at a distal end of the woven mesh are fixed to the plug after being bent from the distal end to a proximal end.

7. The intervention guidance device according to claim 6, wherein the woven mesh comprises a distal-end mesh surface and a proximal-end mesh surface which are integrally connected, the proximal-end mesh surface is closer to the main body portion than the distal-end mesh surface, the mesh wires at the closed end of the distal-end mesh surface pass through the proximal-end mesh surface and then are converged together with the mesh wires at the closed end of the proximal-end mesh surface, and the converged mesh wires are gathered and fixed by the plug.

8. The intervention guidance device according to claim 6, wherein the woven mesh is woven from not less than 16 mesh wires, and a wire diameter of each mesh wire is in a range from 0.0028 inch to 0.0060 inch.

9. The intervention guidance device according to claim 6, wherein the plug is provided with threads for rotational connection with the main body portion.

10. An intervention guidance device, comprising:
a main body portion; and
a guidance portion having a contracted configuration used for delivery and a predetermined expanded configuration, and the guidance portion comprises a woven mesh woven from a plurality of mesh wires and a plug used for gathering and fixing the mesh wires at the closing position of the woven mesh, the mesh wires at a closed end of the woven mesh located at a distal end of the woven mesh are fixed to the plug after being bent from the distal end to a proximal end, and the guidance portion is fixedly connected to a distal end of the main body portion through the plug.

11. The intervention guidance device according to claim 10, wherein the woven mesh comprises a distal-end mesh surface and a proximal-end mesh surface which are integrally connected, the proximal-end mesh surface is closer to the main body portion than the distal-end mesh surface, the mesh wires at the closed end of the distal-end mesh surface pass through the proximal-end mesh surface and then are converged together with the mesh wires at the closed end of the proximal-end mesh surface, and the converged mesh wires are gathered and fixed by the plug.

12. The intervention guidance device according to claim 11, wherein the woven mesh is shaped into a planar disc-shaped structure having a diameter of 10 mm to 25 mm.

13. The intervention guidance device according to claim 11, wherein the cross section of the woven mesh is not circular, and the woven mesh has a radial dimension of 10 mm and 25 mm.

14. The intervention guidance device according to claim 10, wherein the woven mesh is woven from not less than 16 mesh wires, and each mesh wire has a wire diameter of 0.0028 inch to 0.0060 inch.

15. The intervention guidance device according to claim 10, wherein the plug is provided with threads for rotational connection with the main body portion.

* * * * *